United States Patent [19]

Krusic et al.

[11] Patent Number: 5,504,248

[45] Date of Patent: Apr. 2, 1996

[54] PREPARATION OF HALOGENATED COMPOUNDS

[75] Inventors: Paul J. Krusic; Zhen-Yu Yang, both of Wilmington, Del.

[73] Assignee: E. I. Du Pont de Nemours and Company, Wilmington, Del.

[21] Appl. No.: 281,809

[22] Filed: Jul. 28, 1994

[51] Int. Cl.$^6$ .......................... C07C 53/38; C07C 55/36; C07C 255/00; C07C 69/66

[52] U.S. Cl. .......................... 562/849; 562/851; 562/828; 558/447; 560/184

[58] Field of Search .................................. 562/849, 851, 562/828; 558/447; 560/184

[56] References Cited

U.S. PATENT DOCUMENTS 3,862,971  1/1975  Rudolph .................................. 562/851
4,360,645  11/1982  Krespan .................................. 525/403
4,420,038  12/1983  Uschold .................................. 568/415

OTHER PUBLICATIONS

Birchall, J. M. et al, *J. Fluorine Chem.*, 15, 487–495 (1980).

*Primary Examiner*—Paul J. Killos

[57] ABSTRACT

Halogenated compounds are prepared by ring opening reactions of highly fluorinated cyclopropanes with chlorine, bromine, iodine, or mixtures thereof at temperatures over 100° C. A novel compound, which is one type of compound produced, is a highly fluorinated and halogenated ether and other novel compounds are starting materials or products. The products of the process are useful as chain transfer agents for certain free radical polymerizations, and as chemical intermediates in the preparation of various products such as surfactants and textile surface treatments.

18 Claims, No Drawings

PREPARATION OF HALOGENATED COMPOUNDS

FIELD OF THE INVENTION

This invention concerns a process for preparing halogenated organic compounds by the reaction of highly fluorinated cyclopropanes with chlorine, bromine or iodine, or mixtures thereof. Also disclosed are certain novel highly halogenated compounds.

TECHNICAL BACKGROUND

Highly fluorinated cyclopropanes, for instance those which have at least 5 fluorine atoms bound to the carbon atoms of the cyclopropane ring, are known to undergo decomposition reactions, particularly reactions in which difluorocarbene which is formed contains one of the carbon atoms originally part of the cyclopropane ring, see for instance J. M. Birchall, et al., J. Fluorine Chem., vol. 15, p. 487–495 (1980), and references therein. In other words, the ring fragments. To the inventor's knowledge, ring opening reactions in which the three carbon atoms of the cyclopropane ring remain in the same molecule are not known.

SUMMARY OF THE INVENTION

This invention concerns a process for the production of highly halogenated compounds, comprising, contacting a compound of the formula

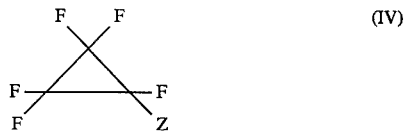

with a compound of the formula XY at a temperature of about 110° C. to about 300° C.; to produce one or both compounds of the formulas $XCF_2CF_2CFYZ$ (I) and $XCF_2CFZCF_2Y$ (II), or compounds of the formulas $QCF_2CF_2C(O)F$ (III) and $QR_f$ (V), wherein:

each X and each Y is independently chlorine, bromine or iodine;

Q is iodine or bromine;

Z is hydrogen, fluorine, chlorine, bromine, iodine, $—R_f$, or $—OR_f$;

$R_f$ is perfluoroalkyl or perfluoroalkyl substituted with one or more of sulfonyl fluoride, nitrile, ester, acyl chloride, acyl fluoride, ether, chlorine or bromine;

and provided that:
  when X and Y are iodine or bromine, Z is $—OR_f$, and said temperature is about 200° C. to about 300° C., (III) and (V) are produced;
  when X and Y are iodine or bromine, Z is $—OR_f$, and said temperature is about 110° C. to about 200° C., one or both of (I) and (II) are produced;
  when at least one of X and Y is chlorine, or when Z is hydrogen, fluorine, chlorine, bromine, iodine, or $—R_f$, said temperature is about 110° C. to about 250° C., one or both of (I) and (II) are produced.

This invention also concerns a compound of the formula $XCF_2CF_2CFYZ$ or $XCF_2CFZCF_2Y$ wherein X and Y are each independently chlorine, bromine or iodine, and Z is $—OR_f$ wherein $R_f$ is perfluoroalkyl or perfluoroalkyl substituted with one or more of sulfonyl fluoride, nitrile, ester, acyl chloride, acyl fluoride, ether, chlorine or bromine.

In addition this invention also concerns a compound of the formula $MCF_2CF(CF_3)OCF_2CF_2T$, (VI), wherein:

M is I—, $ICF_2CF_2CFIO$— or pentafluorocyclopropoxy;

T is $—CO_2R^1$, $—CO_2H$, $—CN$ or $—SO_2F$; and $R^1$ is alkyl containing 1 to 8 carbon atoms.

DETAILS OF THE INVENTION

Disclosed herein are ring opening halogenations (with chlorine, bromine or iodine) of highly fluorinated cyclopropanes. The reaction is carried out at about 110° C. to about 300° C. In most instances the process is run at about 110° C. to about 250° C., preferably about 140° C. to about 200° C. In most of these instances, the product(s) of the reaction is one or both of (I) and (II).

Highly fluorinated cyclopropanes useful herein, include, but are not limited to compounds in which Z is fluorine, hydrogen, chlorine, bromine, trifluoromethyl, heptafluoro-n-propoxy, trifluoromethoxy, hydrogen, pentafluoroethoxy, perfluoro [2-methyl-2(2-fluorosulfonylethoxy)ethoxy], 2-trifluoromethyl-2(-carbomethoxytetrafluoroethoxy)tetrafluoroethoxy, and perfluoro [2-methyl-2(cyanoethoxy)ethoxy]. In preferred highly fluorinated cyclopropanes, Z is fluorine, trifluoromethoxy, pentafluoroethoxy, heptafluoro-n-propoxy, perfluoro [2-methyl-2(2-fluorosulfonylethoxy)ethoxy], 2-trifluoromethyl-2(-carbomethoxytetrafluoroethoxy)tetrafluoroethoxy, and perfluoro[2-methyl-2(cyanoethoxy)ethoxy].

In all of the halogenations one halogen ($Cl_2$, $Br_2$ or $I_2$) can be used, and X and Y are the same. Mixtures of halogens may also be used. It is well known that when such halogens are mixed "interhalogen" compounds such as ICl and IBr are formed. The products of the instant halogenation, when mixtures of halogen as used, are often mixtures of the products of the ring opening reactions from molecules containing only one halogen (i.e. $Cl_2$) and from interhalogen compounds such as ICl. For instance if a mixture of chlorine and bromine is used, the products obtained are often mixtures of halogenations with BrCl, $Cl_2$ and $Br_2$. Examples 4 and 5 illustrate these reactions. In cases where unsymmetrical products can be obtained, either of the halogens may be X or Y.

When $I_2$ or $Br_2$ is used as the halogen, Z is (substituted) perfluoroalkoxy, and the temperature is about 200° C. to about 300° C. a somewhat different product is obtained. This product is the acyl fluoride $QCF_2CF_2C(O)F$ [(III) wherein Q is I or Br]. When $Br_2$ is used as the halogen in this reaction, it is preferred to use temperatures closer to 300° C. than 200° C. It is believed that this product arises from the pyrolysis of a primary product of formula (I) wherein X and Y are iodine or bromine and Z is $—OR_f$. The other product of this particular reaction is $R_fQ$ (V). This process is particularly useful for making the compounds wherein Q is iodine, and especially useful when $R_f$ is trifluoromethyl, pentafluoroethyl, perfluoro-n-propyl, perfluoro[2-methyl-2(2-fluorosulfonylethoxy)ethyl], 2-trifluoromethyl-2(-carbomethoxytetrafluoroethoxy)tetrafluoroethyl, and perfluoro[2-methyl-2(cyanoethoxy)ethyl]. Q in compound (V) will be whatever X and Y were in the compound XY, bromine or iodine. When Z is $—R_f$ or $—OR_f$ it is preferred if these groups have one to 30 carbon atoms. It is also preferred if $—R_f$ is perfluoro-n-alkyl.

The halogenations may be carried out in any type of container which is not substantially affected by the starting materials (especially halogens) or products under the process conditions. The reactions may be carried out in the liquid or gas phase, particularly depending on the volatility of the ingredients, temperature and pressure. The reactions may be carried out in solution in inert solvents such as fluorocarbons, fluorochlorocarbons, and hydrofulorocarbons. Pressure is not critical, autogenous pressure (of all the ingredients, including halogens) being convenient to operate at. The molar ratio of the starting materials is not critical, about stoichiometric quantities (about equimolar amounts) of fluorinated cyclopropane and halogen, or a moderate excess (up to 50% excess) of halogen being preferred. Although not necessary, if the reaction is carried out in the liquid state, moderate agitation is preferred. It is also preferred if oxygen and water are excluded from the reaction. It may be convenient to carry out the reaction under an inert gas blanket, such as nitrogen.

For the compounds $XCF_2CF_2CFYZ$ and $XCF_2CFZCF_2Y$, wherein Z is $—OR_f$, a preferred compound is $XCF_2CF_2CFYZ$. It is more preferred if Z is trifluoromethoxy, pentafluoroethoxy, heptafluoro-n-propoxy, perfluoro[2-methyl-2(2-fluorosulfonylethoxy)ethoxy], 2-trifluoromethyl-2(-carbomethoxytetrafluoroethoxy)tetrafluoroethoxy, or perfluoro[2-methyl-2(cyanoethoxy)ethoxy].

Compounds of the formulas (I) and (II) herein are useful for a variety of purposes. Those in which one or both of X and Y are bromine and/or iodine may be used as chain transfer agents in free radical polymerizations of certain fluorinated vinyl monomers, as described in U.S. Pat. Nos. 4,000,356, 4,158,678, 4,243,770 and 4,361,678. Such iodine and/or bromine containing compounds are also useful as intermediates, such as for making ethylene telomers, and for producing textile treating agent and surfactants, and compounds of formulas (I) and (II) in general are also useful for producing divinyl ethers, alkenyl vinyl ethers or dienes, all of which are useful as gelling agents in the free radical polymerization of fluoromonomers (such types of reactions are illustrated, for instance, in W. A. Sheppard, et al., Organic Fluorine Chemistry, W. A. Benjamin, Inc., New York, 1969. Compounds of formula (III) may also be used as a chain transfer agent that places a reactive group at the end of a polymer chain, useful for chain extension and crosslinking reactions.

Compounds of formula (VI) wherein M is iodine are useful as chain transfer agents in free radical polymerization of various monomers, particularly fluorinated monomers. They are particularly valuable for this purpose since some of the resulting polymer chain ends contain the functional group T which may be used to chain extend or graft the resulting polymer onto another polymer or to react to form a specific chain end which may modify chain end, as to change the polymer's surface properties. Compound (VI) wherein M is $ICF_2CF_2CFIO—$ or pentafluorocyclopropoxy are useful intermediates for making (VI) wherein M is iodine.

Synthesis methods for fluorinated cyclopropanes may be found in P. B. Sargent, et al., J. Am. Chem. Soc., vol. 91, p. 415 et seq. (1969), and P. B. Sargent, J. Org. Chem., vol. 35, p. 678 et seq. (1970). Several of these syntheses are described below as Experiments.

EXAMPLES

EXPERIMENT 1

Preparation of Hexafluorocyclopropane

A 1 L autoclave was charged with 800 g of hexafluoropropylene oxide and heated at 190° C. for 10 hours. Gas (764.5 g) was transferred into a cyclinder and then passed through aqueous NaOH solution and dry tube containing KOH to give 220 g of pure hexafluorocyclopropane, yield 91%. $^{19}F$ NMR: 157.3 (s) ppm.

Example 1

Preparation of 1,3-diiodohexafluoropropane

A 300 mL shaker tube was charged with 25.4 g (0.1 mol) of iodine and 11.0 g (0.073 mol) of hexafluorocyclopropane and heated at 180° C. for 3 hrs and at 210° C. for 4 hrs. After the tube was cooled to room temperature, 11.5 g of iodine was recovered and liquid was diluted with $CFCl_3$, washed with aqueous $Na_2SO_3$. Distillation gave product 18.4 g (62%), bp 75.5° C./150 mmHg. $^{19}F$ NMR: −58.1 (t, J=5.0 Hz, 4F), −105.2 (t, J=5.0 Hz, 2F). Anal: Calcad for $C_3F_6I_2$: C, 8.92; F, 28.23; I, 62.85. Found: C, 9.13; F, 28.12; I, 61.45.

Example 2

Preparation of 1,3-dibromohexafluoropropane

A 300 mL shaker tube was charged with 40 g (0.25 mol) of bromine and 150.0 g of a mixture 37.5 g of hexafluorocyclopropane and 112.5 g trifluoroacetyl fluoride and heated at 240° C. for 20 hrs. After the tube was cooled to room temperature, 37.5 g of crude product was obtained, which was washed with aqueous $Na_2SO_3$. Distillation gave product 29.3 g, bp 72°–74° C. $^{19}F$ NMR: −63.0 (s, 4F), −113.4 (s, 2F). Anal: Calcad for $C_3F_6Br_2$: C, 11.63; Br, 51.58. Found: C, 11.62; Br, 52.12.

Example 3

Preparation of 1,3-dichlorohexafluoropropane

A 300 mL shaker tube was charged with 18.0 g of chlorine and 150.0 g of a mixture 37.5 g of hexafluorocyclopropane and 112.5 g trifluoroacetyl fluoride and heated at 240° C. for 20 hrs. After the tube was cooled to room temperature, 38.8 g of crude product was obtained, which was distilled to give product 29.5 g, bp 35°–36° C. $^{19}F$ NMR: −67.7 (s, 4F), −119.2 (s, 2F). Anal: Calcad for $C_3F_6Cl_2$: F, 51.60. Found: F, 51.91.

Example 4

Reaction of Hexafluorocyclopropane with iodine bromide

A 300 mL shaker tube was charged with 52 g (0.251 mol) of IBr and 40.0 g (0.25 mol) of hexafluorocyclopropane and heated at 240° C. for 20 hrs. After the tube was cooled to room temperature, 69.3 g of crude products were obtained. $^{19}F$ NMR analysis indicated three main products, $BrCF_2CF_2CF_2Br$, $ICF_2CF_2CF_2Br$ and $ICF_2CF_2CF_2I$ in a ratio of 1:4.6:1.3 (mol). Distillation gave 22.3 g of a mixture of $BrCF_2CF_2CF_2Br$ and $BrCF_2CF_2CF_2I$, bp 73°–102° C., 12.0 g of pure $BrCF_2CF_2CF_2I$, bp 103°–104° C., 17.0 g of a mixture of $BrCF_2CF_2CF_2I$ and $ICF_2CF_2CF_2I$, bp 108°–103° C. and 8.4 g of pure $ICF_2CF_2CF_2I$, bp 132° C. $^{19}F$ NMR for $BrCF_2CF_2CF_2I$: −58.6 (m, 2F), −61.3 (m, 2F), −109.3 (m, 2F). Anal: Calcd for $C_3F_6BrI$: C, 10.10; F, 31.95; Br, 22.39; I, 35.56. Found: C, 10.45; F, 31.77; Br, 21.72; I, 36.90.

Example 5

Reaction of Hexafluorocyclopropane with iodine chloride

A 300 mL shaker tube was charged with 16.3 g (0.1 mol) of ICl and 20.0 g (0.125 mol) of hexafluorocyclopropane and heated at 230° C. for 10 hrs. After the tube was cooled to room temperature, 29.2 g of crude products were obtained. $^{19}$F NMR analysis indicated three main products, ClCF$_2$CF$_2$CF$_2$Cl, ICF$_2$CF$_2$CF$_2$Cl and ICF$_2$CF$_2$CF$_2$I in a ratio of 1:1.75:1.5 (mol). Distillation gave 3.9 g of ClCF$_2$CF$_2$CF$_2$Cl, bp 34°–35° C., 3.4 g of a mixture of ClCF$_2$CF$_2$CF$_2$Cl and ClCF$_2$CF$_2$CF$_2$I, bp 40°–79° C., 3.0 g of pure ClCF$_2$CF$_2$CF$_2$I, bp 80°–81° C., 5.5 g of a mixture of ClCF$_2$CF$_2$CF$_2$I and ICF$_2$CF$_2$CF$_2$I, bp 83°–133° C. and 9.8 g of pure ICF$_2$CF$_2$CF$_2$I, bp 133°–135° C. $^{19}$F NMR for ClCF$_2$CF$_2$CF$_2$I: −58.8 (tt, J=13.1 Hz, J=5.0 Hz, 2F), −66.9 (t, J=13.1 Hz, 2F), −112.1 (s, 2F).

EXPERIMENT 2

Preparation of Heptafluoropropanoxypentafluorocyclopropane

A 1 L autoclave was charged with 432 g of CF$_2$=CFOCF$_2$CF$_2$CF$_3$ and 350 g of hexafluoropropylene oxide and heated 190° C. for 8 hrs. The reaction mixture was distilled to give 353.4 g of pure product, bp 55° to 56° C. $^{19}$F NMR: −81.9 (t, J=7.3 Hz, 3F), −87.0 (m, 2F), −130.1 (s, 2F), −152.9 (dt, J=195.5 Hz, J=7.4 Hz, 2F), −155.8 (dm, J=195.7 Hz, 2F), −162.3 (pet, J=8.8 Hz, 1F).

Example 6

Reaction of Heptafluoropropanoxypentafluorocyclopropane with Bromine

A 300 mL shaker tube was charged with 18 g of Br$_2$ and 31.6 g of heptafluoropropanoxypentafluorocyclopropane was heated at 150° C. for 6 hrs. The reaction mixture was washed with aqueous Na$_2$SO$_3$ to give 49.3 g of crude product, which was distilled to give 36.1 g of BrCF$_2$CF$_2$CFBrOCF$_2$CF$_2$CF$_3$, bp 134° to 135° C. $^{19}$F NMR: −61.0 (dt, J=180.3 Hz, J=4.3 Hz, 1F), −63.1 (dd, J=180.8 Hz, J=22.6 Hz, 1F), −71.0 (m, 1F), −81.6 (m, 3F), −83.2 (dm, J=146.5 Hz, 1F), −87.5 (dt, J=dt, J=146.5 Hz, J=7.6 Hz, 1F), −112.3 (m, 2F), −130.3 (m, 2F). Anal: Calcd for C$_6$F$_{12}$Br$_2$O: C, 15.14; F, 47.91; Br, 33.58. Found: C, 14.78; F, 47.75; Br, 32.30.

Example 7

Reaction of Heptafluoropropanoxypentafluorocyclopropane with Iodine

A 300 mL shaker tube was charged with 12.7 g of I$_2$ and 15.8 g of heptafluoropropanoxypentafluorocyclopropane was heated at 165° C. for 4 hrs and 180° C. for 3 hrs. The reaction mixture was washed with aqueous Na$_2$SO$_3$ to give 21.2 g of crude product, which was distilled to give 18.3 g of ICF$_2$CF$_2$CFIOCF$_2$CF$_2$CF$_3$, bp 85°–86° C./40 mmHg. $^{19}$F NMR: −55.3 (d, J=204.6 Hz, 1F), −58.8 (ddd, J=204.6 Hz, J=27 Hz, J=6.3 Hz, 1F), −68.7 (m, 1F), −81.3 to −81.9 (m, 4F), −90.7 (d, J=147.6 Hz, 1F), −102.4 (dt, J=276.7 Hz, J=8 Hz, 1F), −104.4 (dt, J=276.6 Hz, J=7.5 Hz, 1F), −130.4 (s, 2F). Anal: Calcd for C$_6$F$_{12}$I$_2$O: C, 12.65; F, 40.01; I, 44.54. Found: C, 12.57; F, 40.29; I, 45.06.

EXPERIMENT 3

Preparation of Trifluoromethoxypentafluorocyclopropane

A 1 L autoclave was charged with 332 g of CF$_2$=CFOCF$_3$ and 432 g of hexafluoropropylene oxide and heated 200° C. for 8 hrs. 748 g of gas was obtained, which was low temperature distilled to give 329 g of product, bp 6°–7° C. $^{19}$F NMR: −59.5 (d, J=4.6 Hz, 3F), −153.3 (dm, J=J=195.3 Hz, 2F), −155.9 (dm, J=195.8 Hz, 2F ), −163.5 (m, 1F ).

Example 8

Reaction of Trifluoromethoxypentafluorocyclopropane with Bromine

A 300 mL shaker tube was charged with 32 g of Br$_2$ and 50.0 g of trifluoromethoxypentafluorocyclopropane and heated at 180° C. for 8 hrs. After the tube was cooled to room temperature, 63.5 g of crude products were obtained. Spinning band distillation gave 2.5 g of 78°–72° C. cut containing 50% product, 3.6 g of 82°–98° C. cut containing 80% product and 51.3 g of pure product, BrCF$_2$CF$_2$CFBrOCF$_3$, bp 99° C. $^{19}$F NMR: −54.9 (d, J=10.7 Hz, 3F), −60.8 (ddm, J=180.4 Hz, J=5.5 Hz, 1F), −62.8 (ddm, J=180.4 Hz, J=21.1 Hz, 1F), −71.1 (m, 1F), −111.8 (dd, J=274.2 Hz, J=5.4 Hz, 1F), −112.9 (ddd, J=275 Hz, J=7.5 Hz, J=4.3 Hz, 1F). Anal: Calcd for C$_4$F$_8$Br$_2$O: C, 12.78; F, 40.44; Br, 42.52. Found: C, 12.72; F, 42.67; Br, 42.73.

Example 9

Reaction of Trifluoromethoxypentafluorocyclopropane with Iodine

A 300 mL shaker tube was charged with 50 g of iodine and 45 g of trifluoromethoxypentafluorocyclopropane and heated at 150° C. for 4 hrs and 180° C. for 2 hrs. After the tube was cooled to room temperature, 52.3 g of crude products were obtained, which was washed with aqueous Na$_2$SO$_3$ to give 50.3 g of 98% pure product. Distillation gave 44.9 g of 99.9% pure product ICF$_2$CF$_2$CFIOCF$_3$, bp 80°–81° C./100 mmHg. $^{19}$F NMR: −55.0 (dm, J=204.1 Hz, 1F), −55.3 (d, J=11.3 Hz, 3F), −58.4 (ddm, J=205 Hz, J=26.4 Hz, 1F), −68.0 (m, 1F), −102.6 (dt, J=276.2 Hz, J=7.7 Hz, 1F), −104.2 (dt, J=276.4 Hz, J=7.2 Hz, 1F). Anal: Calcd for C$_4$F$_8$I$_2$O: C, 10.23; F, 32.35; I, 54.02. Found: C, 10.99; F, 32.01; I, 53.73.

EXPERIMENT 4

Preparation of Trifluoromethylpentafluorocyclopropane

A 1 L autoclave was charged with 300 g of CF$_2$=CFCF$_3$ and 380 g of hexafluoropropylene oxide and heated 200° C. for 10 hrs. Gas (579 g) was transferred into a cyclinder and then passed through aqueous NaOH solution and dry tube containing KOH to give 283 g of material, which contains low temperature distillation gave product, bp −2° C.

Example 10

Reaction of Trifluoromethylpentafluorocyclopropane with Bromine

A 75 mL shaker tube was charged with 12 g of Br$_2$ and 10 g of trifluoromethylpentafluorocyclopropane and heated at 230° C. for 10 hrs. After the tube was cooled to room temperature, 14.5 g of crude products were obtained. $^{19}$F NMR analysis indicated a mixture of BrCF$_2$CF$_2$CFBrCF$_3$ and BrCF$_2$CFBrCF$_3$ in a 2.3:1 ratio. $^{19}$F NMR for BrCF$_2$CF$_2$CFBrCF$_3$: 60.8 (dm, J=189.1 Hz, 1F), −67.7 (dm, J=189.1 Hz, 1F), −75.9 (m, 3F), −106.6 (dm, J=279.9 Hz, 1F), −109.7 (dm, J=280 Hz, 1F), −139.4 (m, 1F). HRMS: calcd for C$_4$F$_8$Br (M-Br): 278.9056. Found: 278.8938.

Example 11

Reaction of Trifluoromethylpentafluorocyclopropane with Iodine

A 75 mL shaker tube was charged with 25.4 g of $I_2$ and 24 g of a mixture of trifluoromethylpentafluorocyclopropane, $CF_2$=$CFCF_3$ and hexfluorocyclopropane in a 55:25:20 ratio and heated at 230° C. for 10 hrs. After the tube was cooled to room temperature, 22 g of crude products were obtained, which was distilled to give 6.8 g of a mixture of $ICF_2CF_2CF_2I$ and $ICF_2CF_2CFICF_3$, bp 48°–66° C./50 mmHg and 9.6 g of $ICF_2CF_2CFICF_3$, bp 67°–69° C./50 mmHg. $^{19}F$ NMR for $ICF_2CF_2CFICF_3$: −55.6 (dm, J=206.5 Hz, 1F), −57.0 (dm, J=206.5 Hz, 1F), −73.4 (m, 3F), −93.1 (dm, J=279.5 Hz, 1F), −101.2 (dm, J=279.5 Hz, 1F), −143.7 (m, 1F). Anal: Calcd for $C_4F_8I_2$: C, 10.59; F, 33.49; I, 55.92. Found: C, 10.19; F, 33.00; I, 57.71.

EXPERIMENT 5

Preparation of Chloropentafluorocyclopropane A 1 L autoclave was charged with 233 g of $CF_2$5O CFCl and 400 g of hexafluoropropylene oxide and heated 180° C. for 10 hrs. The reaction mixture (528 g) was slowly passed through two −35° C. traps and a −78° C. trap. 246 g of product was collected in the −30° C. traps.

Example 12

Reaction of Chloropentafluorocyclopropane with bromine
A 300 mL shaker tube was charged with 16 g bromine and 22 g of chloropentafluorocyclopropane and heated at 170° C. for 3 hrs and 190° C. for 3 hrs. After the tube was cooled to room temperature, 32.5 g of crude products were obtained, which was distilled by a spinning band to give 9.6 g of bp 73°–114° C. cut containing 63% product and 16.2 g of pure $BrCF_2CF_2CFClBr$, bp 114°–115° C. $^{19}F$ NMR: −58.5 (ddt, J=178.1 Hz, J=10.8 Hz, J=4.6 Hz, 1F), −60.0 (ddm, J=178 Hz, J=16.6 Hz, 1F), −70.8 (m, 1F), −106.7 (dm, J=268.7 Hz, 1F), −109.4 (dm, J=268.1 Hz, 1F). Anal: Calcd for $C_3F_5ClBr_2$: C, 11.04; F, 29.11; halogen calcd as Cl: 32.59. Found: C, 10.53; F, 29.33; halogen calcad as Cl: 32.24.

Example 13

Reaction of Chloropentafluorocyclopropane with Iodine
A 300 mL shaker tube was charged with 25.4 g of iodine and 22 g of chloropentafluorocyclopropane and heated at 170° C. for 3 hrs and 190° C. for 3 hrs. After the tube was cooled to room temperature, 46.3 g of crude products were obtained, which was distilled by a spinning band to give 7.6 g of bp 49.8°–85.6° C./50 mmHg cut containing 51% $ICF_2CF_2CFICl$ and 19.8 g of pure $ICF_2CF_2CFClI$, bp 86°–88° C./50 mmHg. $^{19}F$ NMR: −51.7 (ddd, J=201.9 Hz, J=9.0 Hz, J=6.6 Hz, 1F), −55.8 (ddd, J=201.7 Hz, J=24.8 Hz, J=7.0 Hz, 1F), −72.8 (m, 1F), −94.6 (ddd, J=268.3 Hz, J=13.7 Hz, J=7.0 Hz, 1F), −102.9 (ddd, J=268.3 Hz, J=15.3 Hz, J=9.2 Hz, 1F). Anal: Calcd for $C_3F_5ClI_2$: C, 8.57; F, 22.60; Cl, 8.44; I, 60.39. Found: C, 8.52; F, 22.53; Cl, 7.52; I, 62.27.

EXPERIMENT 6

Preparation bromopentafluorocyclopropane
A 1 L autoclave was charged with 3.5 g of phenothiazine, 161 g of $CF_2$=$CFBr$ and 300 g of hexafluoropropylene oxide and heated 180° C. for 8 hrs. 16 g of bromopentafluorocyclopropane was obtained by low temperature distillation of gas products and 33.5 g of bromopentafluorocyclopropane was obtained by distillation of liquid products, bp 18° to 21° C. $^{19}F$ NMR: −141.7 (dm, J=180 Hz, 2F), −153.0 (dm, J=180.0 Hz, 2F), −172.6 (tt, J=10.1 Hz, J=5.5 Hz, 1F).

Example 12

Reaction of Bromopentafluorocyclopropane with bromine
A 300 mL shaker tube was charged with 10 g bromine and 10.5 g of bromopentafluorocyclopropane and heated at 150° C. for 3 hrs and 180° C. for 3 hrs. After the tube was cooled to room temperature, crude product was washed with aquoues $Na_2SO_3$ solution and distilled to give 11.3 g of a mixture of $BrCF_2CF_2CFBr_2$ and $BrCF_2CFBrCF_2Br$ in a 16.7 to 1 ratio, bp 92°–93° C./200 mmHg. $^{19}F$ NMR for $BrCF_2CF_2CFBr_2$: −58.3 (d, J=15.2 Hz, 2F), −72.3 (tt, J=15.2 Hz, J=13.7 Hz, 1F), −106.2 (d, J=13.7 Hz, 2F). $^{19}F$ NMR for $BrCF_2CFBrCF_2Br$: −54.7 (dm, J=178 Hz, 2F), −56.3 (dm, J=178.1 Hz, 2F), −123.4 (pent, J=15 Hz, 1F).

EXPERIMENT 7

Preparation of pentafluorocyclopropane
A 1 L autoclave was charged with 123 g of $CF_2$=$CFH$ and 273 g of hexafluoropropylene oxide and heated 185° C. for 8 hrs. 383 g of gas was obtained, which was low temperature distilled to give 132 g of product, bp −8° C.

Example 13

Reaction of pentafluorocyclopropane with Iodine
A 75 mL shaker tube was charged with 25.4 g of iodine and 14 g of pentafluorocyclopropane and heated at 190° C. for 3 hours and 210° C. for 2 hrs. After the tube was cooled to room temperature, crude product was washed with aqueous $Na_2SO_3$ to give 24.3 g of material. $^{19}F$ NMR and $^1H$ NMR analysis indicated a mixture of $ICF_2CF_2CFHI$ and $ICF_2CFHCF_2I$ in a 2:1 ratio. Distillation of crude product gave 23.0 g of pure product, bp 85°–86° C./80 mmHg. $^1H$ NMR for $ICF_2CF_2CFHI$: 7.16 (ddd, J=47.6 Hz, J=20.7 Hz, J=1.5 Hz ); for $ICF_2CFHCF_2I$: 4.80 (dtt, J=42.1 Hz, J=14.8 Hz, J=3.3 Hz, 1H). $^{19}F$ NMR for $ICF_2CF_2CFHI$: −52.6 (dm, J=207.8 Hz, 1F), −54.8 (dm, J=207.8 Hz, 1F), −101.0 (ddt, J=273.1 Hz, J=32.3 Hz, J=6.3 Hz, 1F), −116.3 (dm, J=273.1 Hz, 1F), 165.7 (m, 1F); for $ICF_2CFHCF_2I$: −57.9 (dm, J= 207.8 Hz, 2F), −59.8 (dt, J=207.8 Hz, J=6.5 Hz, 2F), −176.2 (m, 1F). Anal: Calcd for $C_3F_5HI_2$: C, 9.34; H, 0.26; F, 24.62. Found: C, 9.00; H, 0.22; F, 24.81. HRMS: calcd for $C_3HF_4I_2$: 385.8088. Found: 385.7962 for $ICF_2CF_2CFHI$ and 385.8171 for $ICF_2CFHCF_2I$.

Example 14

Reaction of pentafluorocyclopropane with Bromine
A 75 mL shaker tube was charged with 18 g of $Br_2$ and 13 g of pentafluorocyclopropane and heated at 190° C. for 3 hrs and 210° C. for 2 hrs. After the tube was cooled to room temperature, crude product was washed with aqueous $Na_2SO_3$ to give 19.3 g of material, which was distilled to give 15.3 g of products, bp 91°–93° C. $^{19}F$ NMR, $^1H$ NMR and GC analysis indicated a mixture of $BrCF_2CF_2CFHBr$, $BrCF_2CFHCF_2Br$ and $BrCF_2CHBrCF_3$ in a 47.1 to 30.3 to 20.8 ratio. $^1H$ NMR for $BrCF_2CF_2CFHBr$: 6.75 (ddt, J=47.3 Hz, J=16.0 Hz, J=1.0 Hz), for $BrCF_2CFHCF_2Br$: 4.97 (dtt, J=42.6 Hz, J=12.2 Hz, J=3.7 Hz), for $CF_2BrCHBrCF_3$: 4.71 (m). $^{19}F$ NMR for $BrCF_2CF_2CFHBr$: −63.6 (dm, J=183.2 Hz, 1F), −64.6 (dm, J=183 Hz, 1F), −111.2 (ddd, J=272.7 Hz, J=20.3 Hz, J=4.7 Hz, 1F), −124.7 (dtd, J=272.7 Hz, J=16.3 Hz, J=9.1 Hz, 1F), −157.3 (m, 1F); for $BrCF_2CFHCF_2Br$: −57.3 (dm, J=166.3 Hz, 2F), −60.4 (dm, J=166.3 Hz, 2F), −187.1 (m, 1F); for $CF_2BrCHBrCF_3$: −48.5 to −50.0 (m, 2F), −66.4 (m, 3F). Anal: Calcd for $C_3F_5HBr_2$: C, 12.35; H, 0.35; F, 32.55; Br, 54.76. Found: C, 12.31; H, 0.20; F, 33.01; Br, 54.34.

EXPERIMENT 8

Preparation of c-$C_3F_5OCF_2CF(CF_3)OCF_2CF_2CO_2CH_3$

A 1 L autoclave was charged with 425 g of $CF_2$=$CFOCF_2CF(CF_3)OCF_2CF_2CO_2CH_3$ and 335 g of hexafluoropropenylene oxide and heated at 185° C. for 10 hrs. Crude products (476.6 g) was distilled to give 391.6 g of pure product, bp 83°–84° C./35 mmHg. $^{19}F$ NMR: −80.4 (s, 3F), −83.5 (m, 2F), −85.2 to −86.4 (m, 2F), −121.6 (s, 2F), −145.7 (t, J=22 Hz, 1F), −152.9 9d, J=193.4 Hz, 2F), −155.7 (dm, J=194 Hz, 2F), −162.4 (t, J=8.7 Hz, 1F). $^1H$ NMR: 3.97 (s). IR (neat): 1791 (s), 1308 (s), 1276 (s), 1239 (s), 1152 (s). Anal: calcd for $C_{10}H_3F_{15}O_4$: C, 25.44; H, 0.64. Found: C, 26.19; H, 0.73.

EXPERIMENT 9

Preparation of c-$C_3F_5OCF_2CF(CF_3)OCF_2CF_2CN$

A 400 mL shaker tube was charged with 150 g of $CF_2$=$CFOCF_2CF(CF_3)OCF_2CF_2CN$ and 128 g of hexafluoropropenylene oxide and heated at 185° C. for 10 hrs. Crude products was distilled to give 75.3 g of pure product, bp 119°–120° C. $^{19}F$ NMR: −80.3 (m, 3F), −84.6 (m, 2F), −85.7 (m, 2F), −108.7 (t, J=5.0 Hz, 2F), −145.1 (t, J=19 Hz, 1F), −152.8 (dm, J=194.3 Hz, 2F), −155.5 (dm, J=194.3 Hz, 2F), −162.4 (t, J=9 Hz, 1F). IR (neat): 2270 (w), 1312(s), 1278 (s), 1248 (s), 1179 (s), 1157 (s), 1121 (s). Anal: calcd for $C_9F_{15}NO_2$: C, 24.62; F, 64.90; N, 3.19. Found: C, 25.03; F, 65.68; N, 2.93.

EXPERIMENT 10

Preparation of c-$C_3F_5OCF_2CF(CF_3)OCF_2CF_2SO_2F$

A 1 L autoclave was charged with 268 g of $CF_2$=$CFOCF_2CF(CF_3)OCF_2CF_2SO_2^F$ and 140 g of hexafluoropropenylene oxide and heated at 185° C. for 10 hrs. Crude products was distilled to give 238.6 g of pure product, bp 91° C./120 mmHg. $^{19}F$ NMR: 30 45.1 (m, 1F), −80.4 (m, 3F), −85.2 (dm, J=143.1 Hz, 1F), −85.9 (dm, J=143 Hz, 1F), −112.4 (s, 2F), −145.2 (t, J=21.5 Hz, 1F), −153.0 (dm, J=201 Hz, 2F), −155.8 (dm, J=201 Hz, 2F), −162.7 (t, J=9 Hz, 1F). IR (neat): 1468 (s), 1278 (s), 1245 (s), 1158 (s), 1139 (s), 987 (s).

Example 15

Reaction of c-$C_3F_5OCF_2CF(CF_3)OCF_2CF_2CN$ with Iodine

A 0.4 L shaker tube was charged with 65 g of c-$C_3F_5OCF_2CF(CF_3)OCF_2CF_2CN$ and 37.6 g of I2 and heated at 150° C. for 2 hrs and 165° C. for 3 hrs. After being washed with aqueous $Na_2SO_3$ solution, 90 g of crude product was obtained which was distilled to give 78.4 g of pure $ICF_2CF_2CFIOCF_2CF(CF_3)OCF_2CF_2CN$, bp 77° C./5 mmHg. $^{19}F$ NMR: −55.4 (d, J=205.1 Hz, 1F), −58.8 (ddd, J=205.5 Hz, J=27.3 Hz, J=5.2 Hz, 1F), −69.4 (m, 1F), −79.1 to −80.4 (m, 4F), −84.1 to −85.2 (m, 2F), −89.9 (dm, J= 152.5 Hz, 1F), 102.0 (dm, J=277.9 Hz, 1F), −104.5 (dm, J=278.4 Hz, 1F), −108.6 (s, 2F), −145.1 (t, J= 21.2 Hz, 0.5F), −145.6 (t, J=21.3, 0.5F). IR (neat): 2269 (w), 1245 (s), 1180 (s), 1125 (s). Anal: Calcd for $C_9F_{15}I_2NO_2$: C, 15.60; I, 36.63; N, 2.02. Found: C, 15.63; I, 37.50; N, 2.14.

Example 16

Reaction of c-$C_3F_7OCF_2CF(CF_3)OCF_2CF_2CO_2CH_3$ with Iodine

A 1 L autoclave was charged with 200 g of c-$C_3F_7OCF_2CF(CF_3)OCF_2CF_2CO_2CH_3$ and 108 g of I2 and heated at 150° C. for 5 hrs. After being washed with aqueous $Na_2SO_3$ solution, the mixtured was checked by GC, indicating 90% of product with 10% of starting material. Distillation of this mixture gave 236.5 g of pure $ICF_2CF_2CFIOCF_2CF(CF_3)OCF_2CF_2CO_2CH_3$, bp 107°–110° C./3 mmHg, and 21.6 g of bp 60°–106° C./3 mmHg material containing starting material. $^{19}F$ NMR: −55.2 (d, J=205.1 Hz, 1F), −58.8 (dm, J=204.4 Hz, 1F), −69.0 (m, 1F), −80.0 (s, 3F), −79.6 to −80.7 (m, 1F), −82.5 to −84.0 (m, 2F), −89.9 (m, 0.5F), −90.3 (m, 0.5F), −102.1 (d, J=277.1 Hz, 1F), −104.6 (dt, J=277 Hz, J=8.4 Hz, 1F), −121.5 (s, 2F), −145.7 (t, J=11.3 Hz, 0.5F), −146.0 (t, J=11.7 Hz, 0.5F). $^1H$ NMR: IR (neat): 2990 (w), 1786 (s), 1306 (s), 1243 (s), 1194 (s), 1152 (s), 1134 (s), 1128 (s). Anal: Calcd for $C_{10}H_3F_{15}I_2O_4$: C, 16.55; H, 0.42; I, 34.96. Found: C, 17.03; H, 0.51; I, 35.21.

Example 17

Reaction of c-$C_3F_5OCF_2CF(CF_3)OCF_2CF_2CO_2CH_3$ with Iodine at higher temperature A 0.4 L shaker tube was charged with 189 g of c-$C_3F_5OCF_2CF(CF_3)OCF_2CF_2CO_2CH_3$ and 100 g of I2 and heated at 150° C. for 3 hrs and 240° C. for 8 hrs. Distillation of the reaction mixture gave 78.3 g of $ICF_2CF_2COF$, bp −58° C. and 129.3 g of $ICF_2CF(CF_3)OCF_2CF_2CO_2Me$, bp 98°–100° C./60 mmHg. $^{19}F$ NMR for $ICF_2CF_2COF$: +28.0 (m, 1F), −62.1 (m, 2F), −111.4 (m, 2F); for $ICF_2CF(CF_3)OCF_2CF_2CO_2Me$: −58.8 (dm, J=210 Hz, 1F), −59.9 (dm, J=210 Hz, 1F), −76.8 (m, 3F), −82.7 (dm, J=158.7 Hz, 1F), −83.7 (dm, J=158 Hz, 1F), −121.6 (t, J=3.3 Hz, 2F), −134.3 (m, 1F). IR for $ICF_2CF_2COF$: 1768 (s), 1187 (s), 1150 (s); IR for $ICF_2CF(CF_3)CF_2CF_2CO_2Me$: 1768 (s), 1342 9s), 1304 (s), 1232 to 1110 (s). Anal: Calcd for $C_7H_3F_{10}IO_3$: C, 18.60; H, 0.67; F, 42.38; I, 28.08. Found: C, 18.24; H, 0.52; F, 42.38; I, 29.46.

Example 18

Reaction of c-$C_3F_5OCF_2CF(CF_3)OCF_2CF_2SO_2F$ with Iodine

A 0.4 L shaker tube was charged with 56 g of c-$C_3F_5OCF_2CF(CF_3)OCF_2CF_2SO_2F$ and 25 g of I2 and heated at 150° C. for 6 hrs. The reaction mixture was poured to a beaker and the tube was washed with 30 mL of $CH_2Cl_2$. The combined organic layers were washed with aqueous $Na_2SO_3$ and NaCl solutions. After removal of the $CH_2Cl_2$, 65.5 g of crude product was distilled to give 59.6 g of pure $ICF_2CF_2CFIOCF_2CF(CF_3)OCF_2CF_2SO_2F$, bp 97° C./4.8 mmHg. $^{19}F$ NMR: +45.3 (m, 1F), −55.6 (d, J=204.7 Hz, 1F), −58.9 (ddd, J=204.7 Hz, J=27.2 Hz, J=6.3 Hz, 1F), −69.3 (m, 1F), −79.3 to −80.2 (m, 6F), −89.8 (dm, J=144.3 Hz, 1F), −101.9 (dm, J=277.9 Hz, 1F), −104.6 (dt, J=277.8 Hz, J=7.7 Hz, 1F), −112.2 (m, 2F), −145.4 (m, 1F). IR (neat): 1465 (s), 1245 (vs), 1198 (s), 1156 (s), 1140 (s), 1121 (s). Anal: Calcd for $C_8F_{16}SO_4I_2$: C, 12.81; F, 40.53; I, 33.84; S, 4.28.

Example 19

Reaction of c-$C_3F_5OCF_2CF(CF_3)OCF_2CF_2SO_2F$ with Iodine at higher temperature A 0.4 L shaker tube was charged with 56 g of c-$C_3F_5OCF_2CF(CF_3)OCF_2CF_2SO_2F$ and 25 g of I2 and heated at 150° C. for 3 hrs and 240° C. for 10 hrs. Distillation of the reaction mixture gave 17.4 g of $ICF_2CF_2COF$, bp 58°–59° C. and 44.3 g of $ICF_2CF(CF_3)OCF_2CF_2SO_2F$, bp 100°–104° C./200 mmHg. $^{19}F$ NMR for $ICF_2CF(CF_3)OCF_2CFSO_2F$: +45.5 (m, 1F), −58.7 (dm, J=213.7 Hz, 1F), −60.0 (dm, J=214 Hz, 1F), −76.9 (m, 3F), −77.9 (dd, J=139.2 Hz, J=22.7 Hz, 1F), −79.7 (dm, J=139.2 Hz, 1F), −122.2 (s, 2F), −133.6 (m, 1F). Anal: Cacld for $C_5F_{11}SO_3$: C, 12.62; I, 26.66. Found: C, 12.68; I, 26.67.

Example 20

Reaction of $c-C_3F_5OCF_2CF(CF_3)OCF_2CF_2SO_2F$ with bromine

A 0.2 L shaker tube was charged with 28 g of $c-C_3F_5OCF_2CF(CF_3)OCF_2CF_2SO_2F$ and 8 g of $Br_2$ and heated at 150° C. for 3 hrs and 250° C. for 20 hrs. The reaction mixture was washed with aqueous $Na_2SO_3$. Crude product (21.8 g) was distilled to give 17.8 g of $BrCF_2CF_2CFBrOCF_2CF(CF_3)OCF_2CF_2SO_2F$, bp 85°–90° C./20 mmHg. $^{19}F$ NMR: +45.2 (m, 1F), −61.1 (d, J=181.1 Hz, 1F), −63.2 (dd, J=181.2 Hz, J=22.9 Hz, 1F), −71.4 (m, 1F), −78.9 to −80.0 (m, 5F), −81.6 to −81.9 (m, 1F), −86.8 (d, J=148 Hz, 1F), −112.2 (m, 2F), −145.4 (m, 1F).

What is claimed is:

1. A process for the production of highly halogenated compounds, comprising, contacting a compound of the formula

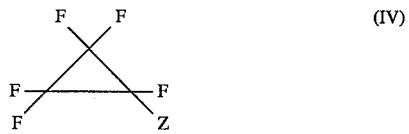 (IV)

with a compound of the formula XY at a temperature of about 110° C. to about 300° C.; to produce one or both compounds of the formulas $XCF_2CF_2CFYZ$ (I) and $XCF_2CFZCF_2Y$ (II), or compounds of the formulas $QCF_2CF_2C(O)F$ (III) and $R_fQ$ (V) wherein:

each X and each Y is independently chlorine, bromine or iodine;

Q is bromine or iodine;

Z is hydrogen, fluorine, chlorine, bromine, iodine, $—R_f$, or $—OR_f$;

$R_f$ is perfluoroalkyl or perfluoroalkyl substituted with one or more of sulfonyl fluoride, nitrile, ester, acyl chloride, acyl fluoride, ether, chlorine or bromine;

and provided that:

when X and Y are iodine or bromine, Z is $—OR_f$, and said temperature is about 200° C. to about 300° C., (III) and (V) are produced;

when X and Y are iodine or bromine, Z is $—OR_f$, and said temperature is about 110° C. to about 200° C., one or both of (I) and (II) are produced;

when at least one of X and Y is chlorine, or when Z is hydrogen, fluorine, chlorine, bromine, iodine, or $—R_f$, said temperature is about 110° C. to about 250° C., one or both of (I) and (II) are produced.

2. The process as recited in claim 1 wherein:

X and Y are iodine or bromine, Z is $—OR_f$, and said temperature is about 110° C. to about 200° C.; or at least one of X and Y is chlorine, or Z is fluorine, chlorine, bromine, iodine, or $—R_f$, or both.

3. The process as recited in claim 2 wherein said temperature is about 140° C. to about 200° C.

4. The process as recited in claim 1 wherein X and Y are the same.

5. The process as recited in claim 3 wherein X and Y are the same.

6. The process as recited in claim 1 wherein X and Y are different.

7. The process as recited in claim 1 carried out in the liquid or gas phase.

8. The process as recited in claim 1 wherein Z is fluorine, chlorine, bromine, trifluoromethyl, heptafluoro-n-propoxy, trifluoromethoxy, hydrogen, pentafluoroethoxy, perfluoro[2-methyl-2(2 -fluorosulfonylethoxy)ethoxy], 2-trifluoromethyl-2(-carbomethoxytetrafluoroethoxy)tetrafluoroethoxy, or perfluoro[2-methyl-2(cyanoethoxy)ethoxy].

9. The process as recited in claim 1 wherein Z is fluorine, trifluoromethoxy, heptafluoro-n-propoxy, pentafluoroethoxy, perfluoro[2-methyl-2(2 -fluorosulfonylethoxy)ethoxy], 2-trifluoromethyl-2(-carbomethoxytetrafluoroethoxy)tetrafluoroethoxy, or perfluoro[2-methyl-2(cyanoethoxy)ethoxy].

10. The process as recited in claim 1 wherein X, Y and Q are iodine, said temperature is about 200° C. to about 300° C., and Z is $—OR_f$.

11. The process as recited in claim 10 wherein $R_f$ is trifluoromethyl, perfluoro-n-propyl, pentafluoroethyl, perfluoro[2-methyl-2(2 -fluorosulfonylethoxy)ethyl], 2-trifluoromethyl-2(-carbomethoxytetrafluoroethoxy)tetrafluoroethyl, or perfluoro[2-methyl-2(cyanoethoxy)ethyl].

12. The process as recited in claim 1 wherein X and Y are iodine, said temperature is about 100° C. to about 200° C., and Z is $—OR_f$.

13. The process as recited in claim 12 wherein $R_f$ is trifluoromethyl, perfluoro-n-propyl, perfluoro-[ 2-methyl-2(2-fluorosulfonylethoxy)ethyl], pentafluoroethyl, 2-trifluoromethyl-2(-carbomethoxytetrafluoroethoxy)tetrafluoroethyl, or perfluoro[2-methyl-2(cyanoethoxy)ethyl].

14. A compound of the formula $XCF_2CF_2CFYZ$ or $XCF_2CFZCF_2Y$ wherein X and Y are each independently chlorine, bromine or iodine, and Z is $—OR_f$, and $R_f$ is perfluoroalkyl or perfluoroalkyl substituted with one or more of sulfonyl fluoride, nitrile, ester, acyl chloride, acyl fluoride, ether, chlorine or bromine.

15. The compound as recited in claim 14 whose formula is $XCF_2CF_2CFYZ$.

16. The compound as recited in claim 15 wherein X and Y are iodine.

17. The compound as recited in claim 14 wherein $R_f$ is trifluoromethyl, perfluoro-n-propyl, perfluoro[2-methyl-2(2-fluorosulfonylethoxy)ethyl], pentafluoroethyl, 2-trifluoromethyl-2(-carbomethoxytetrafluoroethoxy)tetrafluoroethyl, or perfluoro[2-methyl-2(cyanoethoxy)ethyl].

18. A compound of the formula $MCF_2CF(CF_3)OCF_2CF_2T$, (VI), wherein:

M is I—, $ICF_2CF_2CFIO$— or pentafluorocyclopropoxy;

T is $—CO_2R^1$, $—CO_2H$, $—CN$ or $SO_2F$; and $R^1$ is alkyl containing 1 to 8 carbon atoms.

* * * * *